United States Patent [19]

Murray

[11] Patent Number: 5,439,673
[45] Date of Patent: Aug. 8, 1995

[54] HAIR CARE COMPOSITION

[75] Inventor: Andrew M. Murray, Cheshire, United Kingdom

[73] Assignee: Chesebrough-Pond's USA Co., Division of Conopco, Inc., Greenwich, Conn.

[21] Appl. No.: 24,701

[22] Filed: Mar. 1, 1993

[30] Foreign Application Priority Data

Mar. 2, 1992 [GB] United Kingdom ............... 9204509

[51] Int. Cl.6 .......................................... A61K 7/075
[52] U.S. Cl. .............................. 424/70.12; 424/70.11
[58] Field of Search ................................... 424/70, 71

[56] References Cited

U.S. PATENT DOCUMENTS

| | | | |
|---|---|---|---|
| 3,242,218 | 3/1966 | Miller | 568/615 |
| 3,665,041 | 5/1972 | Sianesi et al. | 568/601 |
| 3,715,378 | 2/1973 | Sianesi et al. | 558/283 |
| 3,972,998 | 8/1976 | Keiner | 424/70.16 |
| 4,013,786 | 3/1977 | Cella et al. | 424/63 |
| 4,062,939 | 12/1977 | Scott | 424/70.11 |
| 4,176,176 | 11/1979 | Cella et al. | 424/70.8 |
| 4,183,067 | 1/1980 | Goebel et al. | 132/202 |
| 4,184,973 | 1/1980 | Shaw | 252/174.23 |
| 4,399,077 | 8/1983 | Vanlerberghe et al. | 562/564 |
| 4,523,039 | 6/1985 | Lagow et al. | 568/615 |
| 4,584,196 | 4/1986 | Vanlerberghe et al. | 424/70.8 |
| 4,765,975 | 8/1988 | Iovanni et al. | 424/70.19 |
| 4,778,675 | 10/1988 | Vanlerberghe et al. | 424/70.21 |
| 4,803,067 | 2/1989 | Brunetta et al. | 424/63 |
| 4,880,620 | 11/1989 | Vanlerberghe et al. | 424/70.21 |
| 4,895,876 | 1/1990 | Schweighardt et al. | 514/747 |
| 4,959,171 | 9/1990 | Pantini et al. | 252/174 |
| 4,981,845 | 1/1991 | Pereira et al. | 514/657 |
| 5,093,023 | 3/1992 | Pantini et al. | 252/174.23 |
| 5,160,733 | 11/1992 | Berthiaume | 424/70 |

FOREIGN PATENT DOCUMENTS

| | | |
|---|---|---|
| 0035899 | 9/1981 | European Pat. Off. |
| 0148482 | 7/1986 | European Pat. Off. |
| 0191490 | 8/1986 | European Pat. Off. |
| 0195714 | 9/1986 | European Pat. Off. |
| 0196904 | 10/1986 | European Pat. Off. |
| 0240350 | 10/1987 | European Pat. Off. |
| 0360292 | 3/1990 | European Pat. Off. |
| 0432951 | 6/1991 | European Pat. Off. |
| 0486135 | 5/1992 | European Pat. Off. |
| 0512744 | 11/1992 | European Pat. Off. |
| 55-100308 | 7/1980 | Japan |
| 60-34730 | 2/1985 | Japan |
| 63-107911 | 5/1988 | Japan |
| 6801885 | 5/1968 | Netherlands |
| 1104482 | 2/1968 | United Kingdom |
| 2052537 | 1/1981 | United Kingdom |
| WO88/06434 | 9/1988 | WIPO |

OTHER PUBLICATIONS

European Search Report in the corresponding European Application 93/301503.
Derwent Abstract of EP 0195 714.
Derwent Abstract of JP 60/34730.
Derwent Abstract of JP 55-100308.

*Primary Examiner*—Thurman K. Page
*Assistant Examiner*—Peter F. Kulkosky
*Attorney, Agent, or Firm*—Rimma Mitelman

[57] ABSTRACT

A hair care composition providing good tactile as well as visual hair benefits comprises:
(a) 0.00001 to 0.01% by weight of the composition of a perfluoropolyether material, and
(b) 0.0001 to 0.4% by weight of the composition of a silicone conditioning agent.

6 Claims, No Drawings

HAIR CARE COMPOSITION

FIELD OF THE INVENTION

The present invention relates to hair care compositions, more particularly to compositions which provide a variety of hair conditioning benefits.

BACKGROUND OF THE INVENTION AND PRIOR ART

The art is replete with disclosures of hair care compositions which include one or more conditioning agents for improving one or more of a variety of tactile or visual hair benefits, for example smoothness, softness, shine, anti-static, ease of wet and/or dry combing.

Known conditioning agents for use in hair care compositions include cationic surfactants, volatile or non-volatile silicones, cationic polymers, protein hydrolyzates and quaternised protein hydrolizates, among which silicones are generally the most common. The use of volatile or non-volatile silicones as hair conditioning agents is disclosed for example in EP-A-0 432 951 (Unilever), EP-A-0 240 350 (Procter & Gamble) and EP-A-0 035 899 (Procter & Gamble).

Another material which has recently been proposed, for example in EP-A-03602921, for use as a conditioning agent in hair care compositions is a perfluoropolyether (PFPE) material. The use of low levels of PFPE's in hair conditioning compositions is described in our European Patent publication No. EP-A-0486135.

A problem associated with many known conditioning agents such as those mentioned above is that their use at levels necessary for achieving good tactile benefits like softness and combability is often at the expense of other benefits, for example visual benefits such as shine. Thus, hitherto it has been difficult to achieve good hair benefits over a wide range of tactile and visual descriptors.

SUMMARY OF THE INVENTION

We have now found that by utilising a combination of conditioning agents, each at a low level, it is possible to achieve very good tactile hair benefits such as softness and combability, as well as enhancing visual benefits such as shine.

Accordingly, in a first aspect the present invention provides a hair care composition comprising:
(a) 0.00001 to 0.01% by weight of the composition of a perfluoropolyether material, and
(b) 0.0001 to 0.4% by weight of the composition of a silicone conditioning agent.

DETAILED DESCRIPTION OF PREFERRED EMBODIMENTS

Perfluoropolyether material

The hair care compositions of the invention comprise a perfluoropolyether material. Suitable perfluoropolyethers and their methods of preparation are described in GB 1,104,482, US 3,242,218, US 3,665,041, US 3,715,378, US 4,523,039, EP-A-0,191,490.

Preferred perfluoropolyether materials are homo- or copolymers of the following formula:

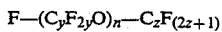
$$F-(C_yF_{2y}O)_n-C_zF_{(2z+1)}$$

wherein
z is an integer from 1 to 6, more preferably 1–3, most preferably 1 or 2;
for each monomer, y is independently selected from the integer-range from 1 to 6, more preferably 1–5, most preferably 1–3;
n indicates the total number of monomers in the polymer backbone and is at least 1, more preferably at least 5, most preferably at least 10.

Since y is independently selected for each monomer unit, polymers of the invention may be homopolymers (if for each monomer y is the same) or copolymers (if at least two values of y are chosen for different monomers).

Most preferably n is selected such that the molecular weight of the polymer is from 100–100,000, more preferably 500–50,000, most preferably 1,000 to 10,000.

Particularly preferred end-groups of the perfluoropolyether (PFPE) material are those wherein z is 1 or 2.

Suitable monomer units for use in the PFPE polymers are for example those disclosed in EP-A-0 360 292. Particularly preferred polymer backbone monomers are those of the group consisting of:
a) $(CF_2-CF_2-O)$
b) $(CF_2-O)$
c) $(C_3F_6-O)$ d) 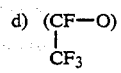
$$\begin{array}{c}(CF-O)\\|\\CF_3\end{array}$$

e) 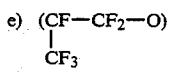
$$\begin{array}{c}(CF-CF_2-O)\\|\\CF_3\end{array}$$

f) $(CF_2-O-CF_2-O)$
g) $(CF_2-O-C_2F_4-O)$;
and mixtures of these monomers.

Particularly preferred polymers comprise a combination of branched polymer unit, for example monomers d) and/or e), with linear monomers, for example a)–c), f) or g). Especially suitable are polymers comprising mixtures of isopropylether groups and methyl ether groups.

Especially preferred examples of PFPE materials are those having the formula:

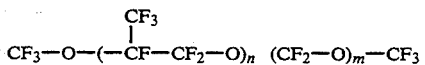
$$CF_3-O-(-\overset{\overset{CF_3}{|}}{CF}-CF_2-O)_n\ (CF_2-O)_m-CF_3$$

wherein the ratio of n to m is from 20 to 40, and wherein preferably the backbone monomers are randomly distributed along the PFPE chain.

Preferred PFPE materials of this formula are those sold under the trade name FOMBLIN HC by Montefluos, for example, FOMBLIN HC/04 (average molecular weight 1500), FOMBLIN HC/25 (average molecular weight 3200) and FOMBLIN HC/R (average molecular weight 6600).

Other suitable materials are those sold under the Demnam trade name ex Daikin Industries Ltd, for example Demnam S-20 having a molecular weight of 2,500, Demnam S-65 having a molecular weight of 4,500, Demnam S-100 having a molecular weight of 5,600 and Demnam S-200 having a molecular weight of 8,400.

If mixtures of backbone monomers are used, preferably the different types of monomers are randomly distributed along the PFPE chain.

The level of PFPE material in the hair care compositions of the invention is low, i.e. from 0.00001 to 0.01%, especially up to 0.008%, more preferably from 0.0001 to 0.008%, most preferably from 0.0001 to 0.005%, by weight of the composition.

Silicone conditioning agent

The hair care compositions of the invention also comprise a silicone conditioning agent, which may be any silicone which enhances tactile or visual properties of hair. The silicone may be present in the composition of the invention in any suitable form, for example in solution, as dispersed insoluble particles or as an emulsion of either insoluble particles or of soluble material dissolved in a solvent.

The silicone conditioning agent is present in the compositions of the invention at a low level compared with prior art silicone-containing hair care compositions, i.e. in an amount of from about 0.0001 to about 0.4%, preferably from about 0.001 to about 0.4%, more preferably from about 0.01 to about 0.3%, by weight of the total composition.

The silicone is preferably selected from volatile silicones, non-volatile silicones and mixtures thereof. Most preferred are non-volatile silicones insoluble in the composition matrix, optionally in combination with a volatile silicone.

Suitable insoluble, non-volatile silicones for use in the invention include one or more of polyalkylsiloxanes, polyarylsiloxanes, polyalkylarylsiloxanes, or mixtures thereof.

Suitable polyalkylsiloxanes include polydimethylsiloxanes which have the CTFA designation dimethicone, having a viscosity of from 5 to 100,000 centistokes at 25° C. These siloxanes are available commercially from the General Electric Company as the Viscasil Series and from Dow Corning as the DC200 Series. The viscosity can be measured by means of a glass capillary viscometer as set out further in Dow Corning Corporate Test Method CTM004 Jul. 20th, 1970. Also suitable are polydiethylsiloxanes.

Polyalkylarylsiloxanes which may be used in the compositions of the invention include polymethylphenylpolysiloxanes having a viscosity of 15 to 65 centistokes at 25° C. These siloxanes are available commercially from the General Electric Company as SF1075 methylphenyl fluid or from Dow Corning as DC556 Cosmetic Grade Fluid.

Also suitable are silicone gums, such as those described in US 4152416 and those available from the General Electric Company under the designations SE30, SE33, SE54 and SE76. "Silicone gum" denotes polydiorganosiloxanes having a molecular weight of from 200,000 to 1,000,000 or more and specific examples include polydimethylsiloxane polymer, polydimethylsiloxane/diphenyl/methylvinyl siloxane copolymer, polydimethylsiloxane/methylvinylsiloxane copolymer and mixtures thereof.

Silicone resins are also suitable for use in the compositions of the invention and are preferably oligomeric alkylpolysiloxanes, arylpolysiloxanes or alkylarylpolysiloxanes, composed of suitable combinations of $R_3SiO_{0.5}$ units, $R_2SiO$ units, $RSiO_{1.5}$ units and $SiO_2$ units. Their ratio is selected so that the resin has average formula $R_nSiO_{[(4-n)/2]}$ where R is $C_{1-6}$ alkyl or aryl and n is from 0.7 to 1.8.

It is preferred that the silicone resin has an average molecular weight of from 500 to 10,000.

Suitable examples of silicone resins useful in the compositions of the invention are Siliconharz MK (ex Wacker) and MQ resin (ex General Electric). Siliconharz MK is a silsesquioxane resin. Resin MQ is prepared by reaction of trimethyl chlorosilane or hexamethyl disilane with silicic or polysilicic acid in the presence of a weak acid in solvent.

A further class of silicone conditioning agents which are useful in the compositions of the invention are the amino functional silicones having the CTFA designation amodimethicone, e.g. trimethylsilylamodimethicone and related compounds, available from Union Carbide.

Another class of silicones suitable for use in the compositions of the present invention are water-insoluble quaternary silicones, which are preferably any polymerised quaternary silicone which is end-functionalised.

Suitably, the end groups may be nitrogen-containing organo-functional end groups, so that charge on the molecule is located at the ends thereof. A suitable type of water-insoluble quaternary silicone has a high chain length, typically of the order of from about 60 to about 120 units, more preferably from about 70 to about 90 units and most preferably of the order of about 80 units.

A typical water-insoluble quaternary polymer may be described by the following formula:

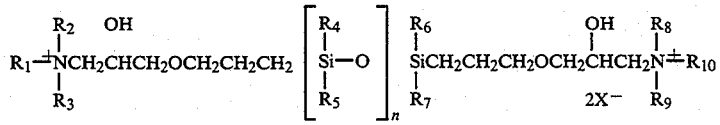

wherein $R_1$ and $R_{10}$ may be the same or different and may be independently selected from hydrogen, saturated or unsaturated long or short chain alk(en)yl, branched chain alk(en)yl, or $C_5$–$C_6$ cyclic ring systems. $R_2$, $R_3$, $R_4$, $R_5$, $R_7$, $R_8$ and $R_9$ may be the same or different and may be independently selected from the group consisting of hydrogen, straight chain or branched lower alk(en)yl, and $C_5$–$C_8$ cyclic ring systems. Preferably the ring systems, if any, have a sufficiently low charge such that the charge on the molecule is concentrated in the organofunctional end groups and the water insolubility of the water insoluble quaternary polymer approximates to at least that of a molecule wherein groups $R_2$–$R_9$ are methyl. Thus, the cyclic groups may be homocyclic or heterocyclic in nature, provided that the water insolubility of the molecule is at least that of a long chain molecule wherein $R_2$–$R_9$ are methyl. Thus, $R_1$, $R_2$–$R_9$ and $R_{10}$ may include nitrogen, oxygen, sulphur, carbon or phosphorus. Preferably, the ring systems comprise homocyclic rings of carbon atoms.

Alternatively, any combination of $R_1$, $R_2$ and $R_3$, and similarly any combination of $R_8$, $R_9$ and $R_{10}$, may form a ring system with the respective end nitrogen of the above formula and so may such systems as morpholine or pyrrolidine.

The value of n may be from about at least 60 or above, but must be such that the water solubility of the quaternary silicone is of the order of less than or equal to 0.01 wt % in water at 20° C. The value of n may be an integer value lying within the range of from about 60 to about 120. Preferably n may be an averaged value of the order of about 80±10, wherein such a value may not be a whole integer value, for example, n may be 80.7 or the like.

The counterion $X^-$ in the above formula is preferably acetate but may instead be for example halide, organic carboxylate, organic sulphonate or the like.

A suitable example of an end-functionalised quaternary silicone is ABIL-QUAT 3274 (ex Goldschmidt), having an n value of about 80, and wherein $R_2$ to $R_9$ are all methyl.

When the silicone conditioning agent in the compositions of the present invention is a volatile silicone, this may be either a cyclic or linear polydiorganosiloxane. Preferably, the polydiorganosiloxane is a polydimethylsiloxane.

The number of silicone atoms in the cyclic silicones is preferably 3 to 7, most preferably 4 or 5. The general formula for cyclic silicones is:

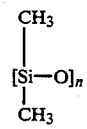

wherein n=3–7. Viscosities of these materials are generally less than 10 centipoise at 25° C.

Linear polydimethylsiloxanes useful in the invention generally have viscosities of less than about 5 centipoise at 25° C. The linear volatile silicones contain preferably from about 3 to about 9 silicon atoms and have the general formula

wherein n=1–7.

Silicones of the above described types are widely available, for example: from Dow Corning as 244, 245, 344, 345 and 200 fluids (cyclopolymethylsiloxane blends), 200/5 fluid (a very short linear polydimethylsiloxane) and 1401 fluid (a mixture of polydimethylsiloxanol gum and cyclopolymethylsiloxanes); from Union Carbide as TP503 fluid (an emulsion of polydimethylsiloxane gum in cyclopolymethylsiloxane) and Silicone 7202 and 7158; and from Stauffer Chemical as SWS-03314.

In the case where a highly viscous silicone is used as the silicone conditioning agent in the invention, incorporation of this material into the composition may be achieved by dissolving the highly viscous silicone in a volatile solvent. As used herein, the term "volatile" means that the material has a measurable vapour pressure.

Preferred solvents are those having a boiling point of from 99° C. to about 260° C. and have a solubility in water of less than about 0.1%. Suitable solvents include the volatile silicones mentioned above and volatile hydrocarbons.

Suitable hydrocarbons include straight chain or branched chain hydrocarbons having from 10 to 16 carbon atoms, preferably from 12 to 16 carbon atoms. Suitable examples are n-dodecane, permethylhydrocarbons 99A and 101A available from Presperse Inc.

If used, the volatile solvent is generally present in an amount of from 0.1 to 10%, preferably from 0.5 to 3% by weight of the total composition.

In preferred embodiments of the compositions in accordance with the invention, the silicone conditioning agent is present as an emulsion, preferably being incorporated in the form of a pre-formed aqueous emulsion.

The emulsion may be prepared by high shear mechanical mixing of the silicone and water, or by emulsifying the insoluble, non-volatile silicone with water and an emulsifier, for example by mixing the silicone into a heated solution of the emulsifier, or by a combination of mechanical and chemical emulsification. Suitable emulsifying agents are well known in the art.

Suitable emulsions also include microemulsions, for example those described in EP-A-0 228 575 and EP-A-0 138 192, the disclosures of which are incorporated herein by reference. Suitable microemulsions formed by the methods of either of these references preferably have particle sizes of 0.15 microns or below, preferably 0.1 microns or below.

Additional components

The hair care compositions in accordance with the present invention may contain one or more additional components, such as surfactants, additional conditioning agents, deposition polymers, suspending agents and optional adjuncts such as perfumes, dyes, buffering agents, thickeners, opacifiers, pearlescers, preservatives, anti-dandruff agents, foam boosters, proteins, moisturising agents and herb or other plant extracts.

The hair care compositions in accordance with the invention may contain one or more surfactants selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other suitable nonionics include mono- or di-alkyl alkanolamides. Examples include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

If desired, the compositions of the invention may also contain one or more additional conditioning agents, preferably selected from cationic surfactants, cationic polymers, protein hydrolyzates and quaternized protein hydrolyzates.

Examples of cationic surfactants include: quaternary ammonium hydroxides, e.g. tetramethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof e.g.
chlorides
Cetylpyridinium hydroxide or salts thereof, e.g. chloride
Quaternium-5
Quaternium-31
Quaternium-18
and mixtures thereof.
Suitable cationic polymers include:
Guar hydroxypropyltrimonium chloride
Poly(dimethyldiallyammonium chloride)
Poly(dimethylbutenyl ammonium chloride)-α, ω-bis(triethanolammonium chloride)
Poly(dipropyldiallylammonium chloride)
Poly(methyl-B-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate)
Poly-Quaternium 7
Poly-Quaternium 10
Poly-Quaternium 11
Poly-Quaternium 22
Poly-Quaternium 16 and mixtures thereof.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

A further optional component of hair care compositions in accordance with the invention is a deposition polymer, preferably a cationic deposition polymer, e.g. a cationic derivative of guar gum.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include those known as JAGUAR C15, having a moderate degree of substitution and a low viscosity, JAGUAR C17 (high degree of substitution, high viscosity) and JAGUAR C16 (which is a hydroxypropylated cationic guar derivative containing a low level of substituent groups as well as cationic quaternary ammonium groups). Also suitable is JAGUAR C162 (which is a high transparency, medium viscosity guar derivative having a low degree of substitution).

If necessary, for example depending upon the identity or form of the PFPE and/or silicone conditioning agents incorporated in the composition according to the invention, one or more suspending agents may further be included in the compositions of the invention.

Suitable suspending agents include polyacrylic acid, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), and heteropolysaccharide gums.

Polyacrylic acid is available commercially as Carbopol 420, Carbopol 488 or Carbopol 943 (ex Goodrich). Suitable polymers of acrylic acid cross-linked with a polyfunctional agent include those available commercially as Carbopol 910, Carbopol 934, Carbopol 940 and Carbopol 941 (ex Goodrich).

An example of a suitable copolymer of a carboxylic acid containing monomer and acrylic ester is Carbopol 1342 (ex Goodrich). Suitable examples of cross-linked polymers of acrylic acid and acrylate esters are Pemulan PR1 and Pemulan PR2. Suitable heteropolysaccharide gums include xanthan gum and guar gums.

A further class of suitable suspending agents are those materials which function as pearlescing agents in cosmetic compositions.

The pearlescing agent may be selected from a wide range of pearlescing agents. Such pearlescing agents may be selected from $C_{16}$–$C_{22}$ fatty acids, $C_{16}$–$C_{22}$ esters of fatty acids with alcohols and $C_{16}$–$C_{22}$ esters of fatty acids incorporating elements such as alkylene glycol units and the like. Suitable alkylene glycol units include ethylene glycol and propylene glycol, though higher alkylene chain length glycols may also be employed. Suitable higher alkylene chain length glycols include polyethylene glycol and polypropylene glycol and the like. Preferably, the pearlescing agent is selected from a wide range of pearlescing agents such as polyethylene glycol mono-or diesters of $C_{16}$–$C_{22}$ fatty acids having from 1 to 7 ethylene oxide units.

Suitable $C_{16}$–$C_{22}$ long chain acyl acids include fatty acids such as stearic acid and behenic acid.

Alternatively, the pearlescing agent may be a long chain acyl derivative material or a mixture of such materials. Ethylene glycol esters of fatty acids having from about 16 to 22 carbon atoms may be suitable.

The pearlescing agent may be a polyethylene glycol mono-or diester such as a member selected from the group stearates, oleates, or myristates. Preferably the polyethylene glycol stearate is a monostearate or distearate.

Preferred esters include polyethylene glycol distearates and ethylene glycol distearates. Examples of polyethylene glycol distearate available commercially are Euperlan PK 900 (ex Henkel) or Genapol TS (ex Hoechst). An example of ethylene glycol distearate is Euperlan PK 810 (ex Henkel).

Crystals of the pearlescing agent may have a thin platelet shape, and when these crystals are dispersed in the hair care composition of the invention, they can help to suspend dispersed particles or droplets of the silicone and/or PFPE by so-called "hindered settling". This contributes to the pearlescent effect observed with such pearlescing agents.

Monomeric ethylene glycol mono- and distearates have been used to suspend particles (e.g. EP 181 773 and EP 34846, both Procter & Gamble). In order to make such compositions it is necessary to heat a mixture of pearlescing agent (A) and surfactant (B) to above the melting/dissolution point of (A) in (B), and then slowly cool the resultant emulsion, whereby platelets of pearlescing agent form.

As a further alternative, the pearlescing agent may be a long chain acyl derivative material or mixture of such materials. Such materials are described in EP 285388 (to Procter and Gamble) and include the ethylene glycol esters of fatty acids having from about 16 to about 22 carbon atoms.

Included are ethylene glycol esters of fatty acids having from about 16 to about 22 carbon atoms. Preferred are the ethylene glycol stearates, both mono and distearate, but particularly the distearate containing less than about 7% of the mono stearate. Other pearlescing agents include alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitae etc.), glyceryl esters (e.g. glyceryl distearate) and long chain esters of long chain alkanol amides (e.g. stearamide DEA distearate, stearamide MEA stearate).

Further suitable pearlescing agents include alkyl ($C_{18-22}$) dimethyl amine oxides such as stearyl dimethyl amine oxide. If the compositions contain an amine oxide or a long chain acyl derivative as a surfactant the suspending function could also be provided and additional suspending agent may not be required if the level of those materials is at least the minimum level given below.

If used, the suspending agent is preferably present in the compositions of the invention in an amount of from about 0.01 to 5% by weight, more preferably from 0.1 to 3% by weight of the total composition.

The hair care compositions of the invention preferably comprise from 20 to 99.5% by weight of water, more preferably 60 to 98%, most preferably 75 to 95%.

The invention is further illustrated, by way of non-limitative example only, by the following Examples.

EXAMPLES

The following conditioning shampoo compositions were prepared by simple mixing of the indicated ingredients in the amounts stated. All amounts given are in % by weight, unless otherwise stated.

TABLE 1

| Ingredient | Example 1 | Example 2 | Example 3 |
|---|---|---|---|
| Sodium lauryl ether sulphate 2EO | 16.0 | 16.0 | — |

TABLE 1-continued

| Ingredient | Example 1 | Example 2 | Example 3 |
|---|---|---|---|
| Sodium lauryl ether sulphate 3EO | — | — | 8.0 |
| Cocoamidopropylbetaine | 2.0 | — | 4.0 |
| Lauryl betaine | — | 2.0 | — |
| PFPE[1] | 0.0003 | 0.0003 | 0.0003 |
| Dimethicone (60,000 cS) | 0.25 | — | — |
| Dimethicone (5,000 cS) | — | 0.3 | — |
| Silicone microemulsion[2] | — | — | 1.6 |
| Jaguar C13S | 0.1 | 0.1 | — |
| Polymer JR 400 | — | — | 0.3 |
| Ethylene glycol distearate | 1.5 | — | — |
| Carbopol 980 | — | 0.4 | — |
| Formalin | 0.1 | 0.1 | 0.1 |
| Colouring, perfume etc. | qs | qs | qs |
| Water | to 100 | to 100 | to 100 |

[1]Fomblin HC/04, HC/25 or HC/R, or Demnam S-20, S-65, S-100 or S-200
[2]Dow Corning X2-1865 (contains 25% wt of silicone)

The following hair conditioner composition was prepared by simple mixing of the indicated ingredients in the amounts stated.

TABLE 2

| Ingredient | Example 4 |
|---|---|
| Cetyltrimethylammonium chloride | 0.5 |
| Cetostearyl alcohol | 3.0 |
| PFPE[3] | 0.0003 |
| Dimethicone (60,000 cS) | 0.25 |
| Hydroxyethylcellulose | 1.0 |
| Colouring, perfume, etc. | qs. |
| Water | to 100 |

[3]as in Examples 1 to 3.

Comparative Examples

A control formulation and various test formulations were prepared, in accordance with the methods of Examples 1 to 4, with the following compositions: Table 3

TABLE 3

| Ingredient | Control | Test Example A | B | C | D |
|---|---|---|---|---|---|
| SLES 2EO | 12.0 | | 16.0 | | |
| Cocoamidopropyl betaine | — | | 2.0 | | |
| Fomblin HC/04 | — | 0 | 0.0003 | 0.0003 | 0 |
| BY 22-026[4] | — | 0.5 | 0 | 0.5 | 4.0 |
| Jaguar C13S | — | | 0.1 | | |
| Ethylene glycol distearate | — | | 1.5 | | |
| Formalin | 0.1 | | 0.1 | | |
| NaCl | 3.0 | | | | |
| Water | to 100 | | to 100 | | |

[4]Silicone emulsion, ex Toray Silicone Co. Ltd, (contains 50% 60,000 cS silicone)

A paired comparison test, the protocol of which is well known in the art, was carried out on the above control and four test formulations for the following hair attributes: softness, ease of dry combing and shine.

The results were as follows:

TABLE 4

| Formulation tested | Score | Significance Level |
|---|---|---|
| Softness | | |
| A vs C | 71 | >99% |
| A vs D | 67 | >99% |
| C vs D | 43 | n.s. |
| Ease of dry combing | | |

TABLE 4-continued

| Formulation tested | Score | Significance Level |
|---|---|---|
| B vs C | 69 | >99% |
| B vs D | 83 | >99% |
| C vs D | 60 | n.s. |
| Shine | | |
| D vs C | 72 | >99% |

*% votes cast for formulation shown on the right
n.s. = no significant difference These results illustrate the surprising result of good enhancement of tactile as well as visual hair benefits by utilising low levels of both PFPE and silicone.

I claim:

1. A conditioning shampoo composition comprising:
   (a) 0.00001 to 0.008% by weight of a perfluoropolyether material having the following formula:

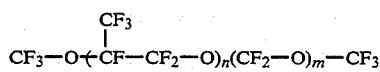

wherein the ration of N to M is from 20 to 40 and N is selected such that the molecular weight of the polymer is from 100 to 100,000

(b) 0.0001 to 0.4% by weight of the composition of a silicone conditioning agent being a non-volatile silicone selected from the group consisting of polyalkylsiloxanes, polyarylsiloxanes, polyalkylarylsiloxanes, silicone gums, silicone resins, aminofunctional silicones and quaternary silicones;
   (c) an anionic surfactant;
   (d) 75-95% by weight of water; and
   (e) a cationic polymer as a deposition aid.

2. A hair care composition according to claim 1, wherein the silicone conditioning agent is a highly viscous silicone dissolved in a volatile solvent.

3. A hair care composition according to claim 1, wherein the silicone conditioning agent is present in the composition in the form of an emulsion.

4. A hair care composition according to claim 1, wherein the silicone conditioning agent is present in an amount of from 0.01 to 0.3% by weight of the composition.

5. A hair care composition according to claim 1 further comprising an ingredient selected from the group consisting of nonionic surfactants, amphoteric surfactants, zwitterionic surfactants, and suspending agents.

6. A method of conditioning hair, comprising applying thereto a hair care composition according to claim 1.

* * * * *